United States Patent [19]

Nochumson

[11] Patent Number: 4,504,641

[45] Date of Patent: Mar. 12, 1985

[54] POLYACRYLAMIDE CROSS-LINKED WITH A POLYSACCHARIDE RESIN AS ELECTROPHORETIC GEL MEDIUM

[75] Inventor: Samuel Nochumson, Rockland, Me.

[73] Assignee: FMC Corporation, Philadelphia, Pa.

[21] Appl. No.: 542,795

[22] Filed: Oct. 17, 1983

Related U.S. Application Data

[63] Continuation-in-part of Ser. No. 350,446, Feb. 19, 1982, abandoned.

[51] Int. Cl.$^3$ .......................... C08L 5/02; C08B 37/12
[52] U.S. Cl. ............................. 526/238.2; 526/238.21; 526/238.22; 526/238.23
[58] Field of Search ........... 526/238.2, 238.21, 238.22, 526/238.23, 238.3; 527/300, 312, 313; 428/221

[56] References Cited

U.S. PATENT DOCUMENTS

| | | | |
|---|---|---|---|
| 2,462,817 | 2/1949 | Smith | 526/238.22 |
| 3,956,273 | 5/1976 | Guiseley | 424/361 |
| 4,060,506 | 11/1977 | Verbanac | 526/238.22 |
| 4,094,832 | 6/1978 | Söderberg | 526/238.22 |
| 4,094,833 | 6/1978 | Johansson et al. | 526/238.22 |
| 4,130,470 | 12/1978 | Rosengren et al. | 204/180 G |

Primary Examiner—John Kight
Assistant Examiner—Nathan M. Nutter
Attorney, Agent, or Firm—Robert D. Jackson; Eugene G. Horsky; Eugene G. Seems

[57] ABSTRACT

An electrophoresis medium, comprising a copolymer of acrylamide and an ethylenically unsaturated resin formed by replacing at least some of the hydroxyl hydrogens in a polysaccharide with an ethylenically unsaturated group, is described.

6 Claims, No Drawings

POLYACRYLAMIDE CROSS-LINKED WITH A POLYSACCHARIDE RESIN AS ELECTROPHORETIC GEL MEDIUM

This is a continuation-in-part of application Ser. No. 350,446, filed Feb. 19, 1982 and now abandoned.

This invention relates to electrophoresis and in particular to an improved polyacrylamide gel electrophoretic carrier medium.

Electrophoresis is the term generally applied to the migration of charged particles through an electrolytic carrier medium under the influence of an electric field. Because of their distinct electrical properties, various classes of charged particles move at different rates through the carrier medium. Those particles having the same electrical properties migrate together in specific, identifiable zones. Electrophoresis has proved an invaluable tool for the resolution and isolation of complex biological substances such as enzymes, serums, carbohydrates and proteins, including albumin and globulins and the like.

Numerous types of carrier media, including free solutions, buffer-saturated paper strips and gels have been used in carrying out electrophoresis. Of these, polyacrylamide gel has been found particularly suitable as an electrophoretic medium. For instance, polyacrylamide gels form highly transparent films, thereby maximizing visibility of the separation bands in the electrogram image. Moreover, acrylamide gels, in either hydrated or dehydrated form, are stable indefinitely. This enables the electrograms to be stored for future reference and study without fear of deterioration. Polyacrylamide gels are strong, insoluble in water, relatively inert and nonionic. By varying the concentration of the polymer, the molecular sieving effect can be controlled. Thus, polyacrylamide gels can be tailored for a given sample in order to resolve particles of specific molecular size.

Polyacrylamide gels, for use as an electrophoretic medium, are obtained by polymerizing acrylamide in the presence of a cross-linking compound such as a divinyl monomer. Polymerization of acrylamide alone produces a linear polyacrylamide which is nongelling. The amount of cross-linker should not exceed about 10% by weight, lest the gel become opaque. Generally, the cross-linker will comprise about 2% to about 5% by weight of the polymerizing mixture. The resulting cross-linked acrylamide is typically used at a gel strength based on a weight/volume ratio corresponding to about 10 g per 100 ml of water. Concentration of the gel will depend on the particular sieving action desired.

N,N'-methylenebisacrylamide is commonly used as the cross-linker in producing polyacrylamide gels, but other divinyl monomers are also satisfactory such as, for instance, ethylene diacrylate, N,N'-(1,2-dihydroxyethylene)-bis-acrylamide, N,N'-diallyltartardimide, N,N',N''-triallylcitric triamide, poly(ethylene glycol) diacrylate 200, N,N'-bis-acrylylcystamine, and poly(ethylene glycol) diacrylate 400. Substituted acrylamides constitute a further class of cross-linkers. Thus, in U.S. Pat. No. 4,189,370 to Boschetti, there are described gel polymers prepared by the radical polymerization of N-methylolacrylamide with a bifunctional allylic or acrylic monomer. The gels were developed as a means of effecting the stepped gradient separation of serum lipoproteins. Anionic polysaccharides containing COOH groups may be added to promote migration of the lipoproteins. In a still further approach, the polyacrylamide is employed in admixture with other gels such as agarose or agar-agar. These mixed gels are disclosed in U.S. Pat. No. 3,573,604 to Uriel.

Electrophoretic gels have been described in which a precursor gel containing vinylic unsaturation is homopolymerized or as an option, copolymerized with a low molecular weight monovinyl compound to form a derivative gel. Thus, in U.S. Pat. No. 4,094,832 to Soderberg, there is disclosed a dextran derivative gel obtained by copolymerizing a dextran derivative containing vinylic groups of the formula:

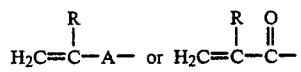

wherein A is —$CH_2$— or —O— and R is a hydrogen, methyl, trifluoromethyl, fluorine, chlorine, bromine or cyano with a vinyl monomer including acrylamide. The amount of vinyl unsaturated dextran can vary from 20 to 100% by weight. In U.S. Pat. No. 4,094,833 to Johansson et al there is described the copolymerization of vinylic unsaturated dextran precursor gel aforesaid with a divinyl compound and optionally a low molecular weight monovinyl compound to give a ternary polymerizate. The resulting gels are obtained in particle form. An exemplary divinyl compound is N,N'-methylenebisacrylamide; acrylamide and substituted acrylamides are illustrative of the low molecular weight vinyl monomers.

The electrophoretic gels of these patents cannot, however, be regarded as polyacrylamide gels as understood and used in the art owing to the large proportion of other components, at least 20% of the dextran derivative according to the Soderberg patent. This greatly exceeds even the upper limit of the 2 to 5% of divinyl cross-linker in conventional polyacrylamide gels; the same applies to the particle gel polymers of Johansson et al. In fact, to produce the dextranase degradable gels of Soderberg, 75 to 95% of the dextran derivative is required. Such biodegradable gels have application in preparatory electrophoresis where enzymatic digestion is a means of releasing and isolating the enclosed substances from the gel matrix. However, the use of such enzymatically digestable gels in analytical electrophoresis is not necessary and may even be a detriment since the dried films bearing the electrogram images are likely to be susceptible to bacterial and fungal attack.

Although a decided advance in the electrophoresis art, polyacrylamide gels are not entirely problem-free. A particularly vexatious trait, for example, is their propensity to pull away from the support base while undergoing dehydration. In fact, the gel by itself shrivels uncontrollably unless special drying precautions are followed. These include careful drying of the gels in a commercial vacuum dryer which ensures constant and controlled heat. Even under these conditions, cracking and shrinkage of the dried films may occur. Some improvement in drying characteristics is afforded by the polyacrylamide/agarose mixtures of Uriel aforesaid provided polyacrylamide gel composition is limited to no more than about 12%; if this gel level is exceeded, shrinking and cracking is again encountered. Even more difficult to dehydrate are the highly concentrated polyacrylamide gels—up to 50% or more—having restricted pore size for use in separating lower molecular weight substances.

It has now been discovered that a polyacrylamide gel, highly resistant to shrinking and cracking on drying, can be realized by polymerizing acrylamide in the presence of a cross-linking agent which is a polysaccharide resin having at least some of the hydroxyl hydrogens replaced by an ethylenically unsaturated group of from 2 to 12 carbon atoms. The provision of said polyacrylamide, its preparation and use as a carrier in electrophoresis, the dried polyacrylamide films bearing an electrophoretic pattern constitutes the principal objects and purposes of the invention. In general, the weight average molecular weight, as determined by light scattering of the polysaccharide resin, will fall within the range of from about 5,000 to about $10^6$ daltons, preferably from about 100,000 to about 500,000 daltons. By ethylenically unsaturated groups is meant those hydrocarbon radicals containing isolated carbon-carbon double bonds which undergo additional polymerization or copolymerization in the presence of a catalyst.

The ethylenically unsaturated polysaccharide resins used in practicing the invention are obtained following known synthetic procedures such as the preparation of modified agarose and agar described in U.S. Pat. No. 3,956,273 to Guiseley. According to this patent, the OH groups in the hydrophilic resins agarose and agar are reacted with acyl and alkylating reagents including ethylenically unsaturated members to provide a variety of resin derivatives. In carrying out these reactions, the resin is first dissolved in strong aqueous alkali, about 0.5 to 1.5 molar in alkali metal hydroxide, after which the ethylenically unsaturated etherification of acylating reagent is added. Examples of etherification agents include alkenyl halides, for example, 3-bromopropene, 3-bromo-2-butene, 4-bromo-2-hexene, 6-bromo-3-heptene, etc; also allylglycidyl ether; acylating agents include acryloyl chloride, crotonyl chloride, methacryloyl chloride, 3-butenoyl, etc. Since some discoloration or darkening of the solution tends to occur during the reaction when it is carried out in aqueous alkaline solution, producing a product which is discolored although otherwise entirely satisfactory, it is also preferred to block the aldehyde end group of the agarose, for example, by reduction before bringing the agar or agarose into contact with aqueous alkali, thus preventing the color-forming reaction which involved the aldehyde group from taking place. The blocking agent of choice is a borohydride, particularly an alkali metal borohydride such as sodium borohydride, which reduces the aldehyde end group to an alcohol (hydroxy) group.

The reaction is preferably carried out at an elevated temperature from about 70° C. to 100° C. or more, but lower temperatures may be used to minimize discoloration if the aldehyde end group is not blocked or to reduce loss when a relatively volatile reagent is used. At lower temperatures, the reaction is slower and in some cases the selected reagent is decomposed by reaction with the water before the desired extent of reaction with agarose can be achieved.

After completion of the reaction, the mixture is cooled to 50° C.–60° C. (if it is at a higher temperature), the alkali is neutralized with an acid or is removed by dialysis or other conventional procedure, and the product is purified by conventional procedures. For example, the solution may be gelled by cooling, frozen and allowed to thaw, then washed and dried, or the product may be precipitated from the reaction solution by mixing with a water-miscible organic liquid which is a non-solvent for the product, such as methanol, ethanol, propanol, acetone, etc. after which the precipitate is filtered, washed with the non-solvent and dried.

These preparations can also be carried out in an organic solvent such as N,N-dimethylformamide, pyridine, or the like, particularly for acylation. Under these conditions, blocking of the aldehyde end group is usually unnecessary, little or no discoloration occurring during the reaction. In addition, acid anhydrides can be employed for acylation instead of acyl halides if desired.

The precise amount of alkenylating or acylating agent employed depends upon the conditions of the reaction and the degree of substitution (D.S.) desired. Usually a large excess above the amount theoretically necessary is used because of the tendency of the agent to react to some extent with water, when present.

Examples of other polysaccharide resins which can be converted into ethylenically unsaturated derivatives, suitable for the practice of the invention include dextran, chitosan, carrageenan, algin, furcellaran, laminarin, locust bean gum, guar gum, methylcellulose, hydroxyethylcellulose, hydroxypropylcellulose, sodium carboxymethylcellulose and the like. In general, any polysaccharide resin having free hydroxyl groups which can be etherified or acylated as above described are suitable candidates for producing the herein electrophoretic compositions. Where an electrically neutral medium is called for, a polysaccharide resin should be selected which is free of ionic groups such as —COOH and —$HSO_4$ radicals.

The electrophoretic compositions of the invention are prepared generally following the known procedures of forming cross-linked polyacrylamide gel matrices. Thus a mixture of acrylamide and a cross-linking amount, normally no more than about 5% by weight based on the mixture, typically about 3% of the herein ethylenically unsaturated polysaccharide resin is dissolved in a buffered solution containing a polymerization catalyst such as N,N,N',N'-tetramethylethylene diamine (TEMED) and an initiator such as ammonium persulfate, and the requisite aliquot then transferred to a molding cassette provided with a suitable support sheet such as polyester film having an activated surface to promote adhesion of the gel. After polymerization is complete, the gel coating is used in carrying out electrophoretic separations and then processed in the usual manner. The finished gel can be dried directly in an oven with no evidence of shrinking or cracking and with excellent preservation of the electrophoretic pattern.

Reference is now made to the following examples

SYNTHESIS OF DERIVATIZED POLYOLS

Example 1

Allylglycidylagarose

Agarose (10 grams) is dissolved in 490 ml of boiling water. The solution is maintained at 80° C. and 10 ml of 4.4M sodium borohydride in 14M sodium hydroxide is added with constant stirring. After 10 minutes, 100 ml of a 10% sodium hydroxide solution is added, followed by the drop-wise addition of 25 ml of allylglycidyl ether over a 15-minute period. After one hour, an additional 25 ml of allylglycidyl ether is added as before and reacted for another hour. The reaction mixture is cooled to 60° C. and then neutralized by the addition of 4M acetic acid as indicated by phenolphthalein. The solution is slowly added to 3 volumes of isopropanol, yielding a white precipitate, which is recovered by filtering through a dacron cloth. After two washings in 2 liters of 60% isopropanol, the precipitate is oven dried overnight at 60° C. and ground to a fine powder. The derivatized agarose had its initial gelling temperature (42° C.) lowered to 16° C.

Example 2

Allylglycidyldextran

Fifty grams of dextran (MW ~250,000) is dissolved in 500 ml of water and heated to 80° C. in a constant water bath. The solution is maintained at 80° C. and 15 ml of 4.4M sodium borohydride in 14M sodium hydroxide is added with constant stirring. After 10 minutes, 100 ml of a 25% sodium hydroxide solution is added, followed by the drop-wise addition of 50 ml of allylglycidyl ether over a 30-minute period. After two hours, an additional 25 ml of allylglycidyl ether is added and the reaction allowed to continue for another two hours. The reaction mixture is cooled to 60° C., and then neutralized by the addition of 4M acetic acid as indicated by phenolphthalein. The solution is slowly added to three volumes of isopropanol, yielding a white gelatinous precipitate. This is cooled down to 0° C. and the alcohol decanted off. The solidified precipitate was redissolved in 500 ml of water at 60° C. and again added to 3 volumes of IPA and cooled to 0° C. The solidified precipitate was recovered after decanting and oven dried overnight at 60° C. and ground to a fine powder.

Example 3

Electrophoresis Using Polyacrylamide/Allylglycidylagarose Gel

A 30% (w/v) solution of acrylamide was prepared in distilled water. Two grams of allylglycidylagarose were dissolved in a final volume of 50 ml of distilled water by heating to boiling and then cooling to room temperature. Fifty ml of a 1.5M Tris-HCl (pH 8.8), 0.4% sodium dodecylsulfate, 0.1% tetramethylethylenediamine solution was then added to the allylglycidylagarose solution to yield a 2% (w/v) solution of the derivatized agarose. Finally, 10 ml of the 30% acrylamide solution was added to 10 ml of the 2% allylglycidylagarose solution plus 14 mg of ammonium persulfate. This acrylamide/allylglycidylagarose solution was then added to a casting apparatus for formation of the copolymer gel. The casting apparatus consisted of a rectangular glass plate (15.9 cm × 14 cm) and a notched glass plate supplied by Aquebogue Machine and Repair Shop (Aquebogue, Long Island, N.Y.). A sheet of Gel-Bond ® PAG was placed on top of the rectangular glass plate so that the hydrophilic side was facing outwards. Three plastic spacers, 1.2 mm thick were placed in a U-shaped configuration over the edges of the glass-supported plastic and the notched glass plate placed on the spacers and held in place with six spring clamps. Following polymerization and gel formation of the acrylamide/allylglycidylagarose solution, a stacking gel was prepared by layering on top of the previous gel 10 ml of a 0.125 M Tris-HCl (pH 6.8) solution containing 3% acrylamide, 2.6% N,N'-methylenebisacrylamide, 0.1% sodium dodecylsulfate, 0.025% tetramethylethylenediamine and ammonium persulfate. Sample slots were formed using a teflon comb and following polymerization of the stacking gel, the glass cassette is placed into an electrophoretic chamber manufactured by Aquebogue Machine and Repair Shop. Protein samples ranging in molecular weight from 17,000 to 200,000 daltons were prepared at a concentration of 1 mg/1 ml in 0.625 Tris-HCl (pH 6.8) containing 2% sodium dodecylsulfate, 10% glycerol, 5% 2-mercaptoethanol and 0.001% bromophenol blue and 5 μl aliquots were added to the sample wells. The upper and lower reservoirs contained 0.025M Tris, 0.192M glycine and 0.1% sodium dodecylsulfate (pH 8.3). Electrophoresis was carried out at 25 mAmps for 2.5 hours. The polyacrylamide/allylglycidylagarose gel was removed from between the glass plates firmly attached to the Gel-Bond ®PAG plastic support. It was placed in a staining solution consisting of 0.05% Coomassie brilliant blue R-250 in 25% isopropanol, 10% acetic acid overnight. The gel was destained for 8 hours in a solution of 45% methanol, 45% acetic acid and then placed in a solution of 7% acetic acid, 5% glycerol for 2 additional hours. After this time, the protein bands were visible and the gel was placed directly in an oven at 65° C. until a flexible dried film formed. This dried gel maintained a definitive protein band pattern with no shrinkage or distortion and was kept in a lab notebook as a permanent record.

Example 4

Electrophoresis Using Polyacrylamide/Allylglycidyldextran

Electrophoresis is performed as described in Example 3 with the exception that the polyacrylamide/allylglycidylagarose gel is replaced by a polyacrylamide/allylglycidyldextran gel. This gel consisted of 15% acrylamide, 5% allylglycidyldextran (from Example 2) in 0.375M Tris-HCl (pH 8.8), 0.1% sodium dodecylsulfate, 0.025% tetramethylethylenediamine and ammonium persulfate. Following electrophoresis, staining, and destaining, the gel was dried to a thin film on the Gel-Bond ® PAG support by direct oven drying at 65° C.

What is claimed is:

1. An electrophoretic gel composition comprising polyacrylamide cross-linked with a polysaccharide resin having a weight average molecular weight of from about 5000 to about $10^6$ daltons and wherein there has been substituted for at least some of the hydroxyl hydrogens in said resin an ethylenically unsaturated group of from 2 to 12 carbon atoms capable of cross-linking with acrylamide in the presence of a catalyst to form said cross-linked polyacrylamide.

2. The composition of claim 1 wherein the ethylenically unsaturated group is selected from the class consisting of aliphatic hydrocarbon and acyl groups.

3. The composition of claim 1 wherein the polysaccharide is agarose.

4. The composition of claim 1 wherein the polysaccharide is dextran.

5. An electrophoretic gel composition comprising polyacrylamide cross-linked with allylglycidylagarose.

6. An electrophoretic gel composition comprising polyacrylamide cross-linked with allylglycidyldextran.

* * * * *